US005801024A

United States Patent [19]
van den Brink et al.

[11] Patent Number: 5,801,024
[45] Date of Patent: Sep. 1, 1998

[54] OXIDOREDUCTASE FROM FILAMENTOUS FUNGI, DNA CODING THEREFOR AND CELLS TRANSFORMED WITH SAID DNA

[75] Inventors: Johannes Maarten van den Brink, Utrecht; Robertus Franciscus van Gorcom, Delft, both of Netherlands

[73] Assignee: Nederlandse Organisatie voor toegepast-natuurwetenschappelijk onderzoek TNO, Netherlands

[21] Appl. No.: 553,279

[22] PCT Filed: Jun. 10, 1994

[86] PCT No.: PCT/NL94/00135

§ 371 Date: Nov. 28, 1995

§ 102(e) Date: Nov. 28, 1995

[87] PCT Pub. No.: WO94/29453

PCT Pub. Date: Dec. 22, 1994

[30] Foreign Application Priority Data

Jun. 11, 1993 [NL] Netherlands ............... 9301025

[51] Int. Cl.⁶ .................. C12P 7/00; C12P 7/40; C12N 9/02; C07H 21/04
[52] U.S. Cl. ............ 435/132; 435/136; 435/189; 435/190; 435/191; 435/254.11; 435/254.3; 435/252.3; 435/320.1; 435/325; 536/23.2; 935/22
[58] Field of Search ................... 435/189, 190, 435/191, 132, 136, 320.1, 254.3, 254.11, 325; 536/23.2, 23.7, 23.74; 935/22

[56] References Cited

PUBLICATIONS van Gorcom et al. (1990) Isolation and molecular characterisation of the benzoate–para–hydroxylase gene (bphA) of Aspergillus niger: A member of a new gene family of the cytochrome P450 superfamily, Mol. Gen. Genet. 223: 192–197, Dec. 1990.

Ngo et al. (1994) Computational Complexity, Protein Structure Preticition, and the Levinthal Paradox, In The Protein Folding Problem and Tertiary Structure Prediction, Eds. Merz et al., Birkhauser, Boston, MA, pp. 491–495, Jan. 1994.

van den Brink et al. (1995) Cloning and Characterization of the NADPH Cytochrome P450 Oxidoreductase Gene from the Filamentous Fungus Aspergillus niger, DNA and Cell Biology 8(14):719–729, Aug. 1995.

*Primary Examiner*—Robert A. Wax
*Assistant Examiner*—Einar Stole
*Attorney, Agent, or Firm*—Londa and Traub LLP

[57] ABSTRACT

Disclosed is a new gene which codes for a NADPH cytochrome P450 oxidoreductase from filamentous fungi. Also disclosed are a recombinant DNA molecule which comprises at least a part of that gene, an RNA molecule derived therefrom and a new polypeptide (or protein), as well as at least one host cell transformed with such recombinant DNA molecule. Particularly suitable host cells are those originating from a filamentous fungus. With the polypeptides (proteins) and the host cells according to the invention, new processes for enzymatic conversions can be performed. In particular, enzymatic conversions by means of monooxygenases, more particularly by means of enzymes from the cytochrome P450 superfamily are improved with the invention.

13 Claims, 5 Drawing Sheets

| | | | | | |
|---|---|---|---|---|---|
| TGATAACTCC | TCAGCAAATC | GGAGTAAACA | GAAGGACAAG | TCATTGGAGT | ACTAAGTAGC | 60 |
| TCCGTGTCAG | AGACCCGGAC | AGGATCAGCT | TCTCCGAACC | CGAGACTCCG | GGCGAAAAGG | 120 |
| CCACCATCGC | TCAGGCTACC | ACCTGTGTTC | CTTCCGTCGA | TCGTCCTCCC | TCGTTTCCGG | 180 |
| CTCACGGCCC | CCCAAATTAT | TGCGGTCTGC | TTAGCAGTGG | GTTCGGCCTC | TCTGTTCTTC | 240 |
| CTGGATCACA | CCACGGCTTA | CTTTCTTATC | CTTTTCCTTT | TCCTTTCTTC | CTTTCTTCCT | 300 |
| GTTCTCCTTT | CTTCCTTTCC | ACCCCCTTCT | TTCTTTTAAC | CCCATAGCGT | CATTCTTTCT | 360 |
| TCCGTTTTAT | CTTTGGTTTT | GGGACGCCGC | CACCTTATCT | CGGTTCCTGC | CTCGGTCTCC | 420 |
| GGTGATCGCA | CCTGGATAGG | CTAAGCGTAG | GGAGGTGTGA | CATTCTTCTT | TCACCTCCTC | 480 |
| TCCTTTTCCC | GCCTCACTCC | GTTCAATCCC | CCGCTCCACC | CTTTCAGACT | CGCCATCGTA | 540 |
| TCAAGTCGGG | GCCTTTGCTT | GCGCCGCTGA | ACAGCCTCAC | CATGGCGCAA | CTCGATACCC | 600 |
| TCGATCTGGT | GGTCCTGGCG | GTGCTTTTGG | TGGGTAGCGT | GGCCTACTTC | ACCAAGGGCA | 660 |
| CCTACTGGGC | AGTTGCAAAG | ACCCGTATGC | CTCTACCGGC | CCGCGGATG | AACGGCGCCG | 720 |
| TTAAGGCTGG | CAAGACTCGG | AACATCATTG | AGAAGATGGA | AGAAACGGGC | AAGAATTGTG | 780 |
| TTATTTTCTA | CGGATCGCAA | ACTGGAACCG | CTGAGGACTA | CGCCTCCAGA | TTGGCCAAGG | 840 |
| AAGGATCTCA | GCGCTTCGGC | CTCAAGACCA | TGGTGGCTGA | CCTCGAGGAA | TACGACTATG | 900 |
| AGAACCTGGA | CCAATTCCCG | GAGGACAAGG | TTGCGTTTTT | CGTGCTCGCC | ACCTACGGAG | 960 |
| AGGGTGAGCC | TACGGATAAT | GCTGTTGAGT | TCTACCAGTT | CTTCACCGGT | GACGACGTTG | 1020 |
| CTTTTGAGAG | CGCGTCCGCG | GACGAGAAGC | CTCTGTCCAA | GCTGAAGTAT | GTTGCTTTCG | 1080 |
| GTCTGGGTAA | CAACACTTAT | GAGCACTACA | ACGCCATGGT | TCGTCAAGTC | GATGCTGCTT | 1140 |
| TCCAGAAGCT | CGGGCCGCAG | CGTATTGGTT | CTGCTGGCGA | GGGTGATGAC | GGTGCCGGTA | 1200 |
| CAATGGAAGA | AGACTTCTTG | GCCTGGAAGG | AGCCCATGTG | GGCAGCACTG | TCGGAGTCGA | 1260 |
| TGGATCTCGA | AGAGCGTGAA | GCGGTCTACG | AACCTGTTTT | CTGCGTCACC | GAAAACGAGT | 1320 |
| CCCTGAGCCC | TGAGGACGAG | ACGGTCTATC | TTGGAGAGCC | CACCCAGAGC | CACCTTCAGG | 1380 |
| GTACTCCCAA | AGGCCCGTAC | TCTGCGCACA | ACCCCTTTAT | CGCCCTATT | GCCGAATCTC | 1440 |
| GTGAGCTTTT | CACCGTCAAG | GATCGCAACT | GTCTGCACAT | GGAAATTAGC | ATCGCTGGAA | 1500 |
| GTAACTTGTC | CTACCAGACT | GGTGACCACA | TCGCTGTTTG | GCCCACAAAC | GCTGGTGCCG | 1560 |
| AAGTGGATCG | GTTCCTTCAG | GTCTTCGGTC | TCGAGGGCAA | GCGTGATTCG | GTCATCAACA | 1620 |
| TCAAGGGTAT | CGATGTTACG | GCCAAGGTCC | CAATCCCGAC | CCCGACCACG | TACGATGCCG | 1680 |
| CTGTTCGGTA | CTATATGGAA | GTCTGCGCCC | CTGTGTCCCG | TCAGTTTGTA | GCCACTCTGG | 1740 |
| CCGCGTTCGC | TCCGATGAGG | AAAGCAAGGC | AGAGATTGTG | CGTCTGGGTA | GCACAAGGAC | 1800 |
| TATTTCCACG | AGAAGGTCAC | CAACCAATGC | TTCAACATGC | CCAGGCTCTT | CAGAGCATCA | 1860 |
| CGTCCAAGCC | TTTCTCTGCT | GTTCCGTTCT | CTCTGCTTAT | TGAAGGCATT | ACGAAGCTGC | 1920 |
| AGCCTCGCTA | CTACTCGATC | TCTTCGTCCT | CCCTTGTCCA | GAAGGACAAG | ATCAGCATCA | 1980 |
| CGGCCGTTGT | GGAATCTGTT | CGTCTGCCCG | GTGCCTCTCA | CATGGTGAAG | GGTGTGACTA | 2040 |

FIG.1

Thr Ala Lys Val Pro Ile Pro Thr Pro Thr Thr Tyr Asp Ala Ala Val
        355             360             365

Arg Tyr Tyr Met Glu Val Cys Ala Pro Val Ser Arg Gln Phe Val Ala
    370             375             380

Thr Leu Ala Ala Phe Ala Pro Met Arg Lys Ala Arg Gln Arg Leu Cys
385             390             395                         400

Val Trp Val Ala Gln Gly Leu Phe Pro Arg Glu Gly His Gln Pro Met
                405             410                 415

Leu Gln His Ala Gln Ala Leu Gln Ser Ile Thr Ser Lys Pro Phe Ser
            420             425             430

Ala Val Pro Phe Ser Leu Leu Ile Glu Gly Ile Thr Lys Leu Gln Pro
        435             440             445

Arg Tyr Tyr Ser Ile Ser Ser Ser Ser Leu Val Gln Lys Asp Lys Ile
    450             455             460

Ser Ile Thr Ala Val Val Glu Ser Val Arg Leu Pro Gly Ala Ser His
465             470             475                         480

Met Val Lys Gly Val Thr Thr Asn Tyr Leu Leu Ala Leu Lys Gln Lys
            485             490             495

Gln Asn Gly Arg Ser Leu Ser Arg Pro Ser Arg Leu Asp Leu Leu His
        500             505             510

His Gly Pro Arg Asn Lys Tyr Asp Gly Ile His Val Pro Val His Val
        515             520             525

Arg His Ser Asn Phe Lys Leu Pro Ser Asp Pro Ser Arg Pro Ile Ile
    530             535             540

Met Val Gly Pro Gly Thr Gly Val Ala Pro Phe Arg Gly Phe Ile Gln
545             550             555                         560

Glu Arg Ala Ala Leu Ala Ala Lys Gly Glu Lys Val Gly Pro Thr Val
                565             570             575

Leu Phe Phe Gly Cys Arg Lys Ser Asp Glu Asp Phe Leu Tyr Lys Asp
            580             585             590

Glu Trp Lys Thr Tyr Gln Asp Gln Leu Gly Asp Asn Leu Lys Ile Ile
        595             600             605

Thr Ala Phe Ser Arg Glu Gly Pro Gln Lys Val Tyr Val Gln His Arg
    610             615             620

Leu Arg Glu His Ser Glu Leu Val Ser Asp Leu Leu Lys Gln Lys Ala
625             630             635                         640

Thr Phe Tyr Val Cys Gly Asp Ala Ala Asn Met Ala Arg Glu Val Asn
                645             650             655

Leu Val Leu Gly Gln Ile Ile Ala Ala Gln Arg Gly Leu Pro Ala Glu
            660             665             670

Lys Gly Glu Glu Met Val Lys His Met Arg Arg Arg Gly Arg Tyr Gln
        675             680             685

Glu Asp Val Trp Ser
690

FIG.2

OXIDOREDUCTASE FROM FILAMENTOUS FUNGI, DNA CODING THEREFOR AND CELLS TRANSFORMED WITH SAID DNA

BACKGROUND OF THE INVENTION

The invention relates to a new gene, a recombinant DNA molecule comprising at least a part of that gene, an RNA molecule derived therefrom and a new polypeptide (or protein), as well as a host cell transformed at least with such recombinant DNA molecule, in particular a transformed filamentous fungus. In addition, the invention relates to processes for the use of the new protein or the new host cell in enzymatic conversions using monooxygenases, more specifically enzymes from the cytochrome P450 superfamily.

In particular, the invention relates to the isolation, characterization and use of a gene coding for an NADPH cytochrome P450 oxidoreductase from filamentous fungi. Further, this application discloses the use of this gene for increasing cytochrome P450-mediated enzymatic activities.

In nature, monooxygenase reactions are responsible for a large number of conversions of both endogenous and exogenous compounds. The monooxygenases can be divided into many different classes of enzymes. One of those classes is the family of cytochrome P450 monooxygenases. These are enzymes occurring in both prokaryotes and eukaryotes.

The spatial structure of these proteins has been highly conserved during evolution. The most characteristic part of each cytochrome P450 is the presence of a haem group which is covalently bound to the protein by a sulfur-iron bond. The sulfur always originates from a cysteine molecule. The iron atom is located in the middle of a porphyrin ring with which the atom has four bonds. The sixth ligand of the iron atom is involved in the catalysis of the reaction. An oxygen is bound to it during the process. Accordingly, the manner in which the haem group is bound to the protein is characteristic of this class of proteins and provides for a specific absorption peak at approximately P450 nanometer (CO reduced form).

Cytochrome P450 proteins are only functional in an enzyme complex together with one or two other proteins which take care of the transfer of electrons from NAP(P)H to the active center of the cytochrome P450.

Roughly, the class of cytochrome P450 enzyme systems can be divided in two subclasses, viz. the eukaryotic microsomal P450s and the class of "prokaryotic-like" P450s. The general characteristics of the eukaryotic microsomal P450s are that they are bound to the membranes of eukaryotes, that they are two component enzyme systems (reaction specific cytochrome P450 and general NADPH cytochrome P450 oxidoreductase) and that the reaction is NADPH-dependent. The general characteristic of the other subclass is that the enzyme complexes consist of three components. This subclass can be further subdivided in two groups, viz. the bacterial P450s (soluble, mostly NADH dependent, complex consisting of a reaction specific cytochrome P450 and a general Fe-S protein and NADH reductase) and the eukaryotic P450s occurring in organelles such as mitochondria (membrane-bound, mostly NADPH dependent, complex consisting of reaction specific cytochrome P450 and a general Fe-S protein and NAD(P)H reductase).

The cytochrome P450 proteins of the first subclass accordingly complex to the membrane with the protein NADPH cytochrome P450 oxidoreductase. This protein, like cytochrome P450s, is found in the microsomal (endoplasmatic reticulum) membrane of lower eukaryotes, plants and animals.

Less is known about the structure of this protein than about that of cytochrome P450s, but here, too, a high degree of structural conservation must have occurred during the evolution, in view of the fact that functional exchange of NADPH cytochrome P450 oxidoreductase has been demonstrated between yeast and mammal systems.

In microsomal enzyme systems of various eukaryotes, it has been demonstrated in different cases that particularly after induction of a specific cytochrome P450, the oxidoreductase could be present in a minor proportion. Thus, the amount of reductase would be determinative or the rate of conversion of compounds to be modified by cytochrome P450. Increasing the amount of NADPH cytochrome P450 oxidoreductase in the cell could then increase the biocatalytic activity (in respect of reactions catalyzed by P450s).

To date, little is known about cytochrome P450 enzyme systems in filamentous fungi. Only a few cytochrome P450 enzymes have been characterized and rather little knowledge is available about the way of electron transfer from NADPH to the cytochrome P450. It has been demonstrated that with fungi, too, the transfer of electrons occurs most probably through a NADPH cytochrome P450 oxidoreductase. In this connection, use was made of immunological and biochemical experiments (Scala, Matthews, Costa & Van Etten (1988) Experimental Mycology 12, 377–385). They show in this article that NADPH cytochrome P450 oxidoreductases of other filamentous fungi can complement the endogenous NADPH cytochrome P450 oxidoreductase in reconstitution experiments with pisatin demethylase from *Nectria haematococca* (CYP 57) using an in vitro pisatin demethylase assay.

These authors further show an immunological relationship between the NADPH cytochrome P450 oxidoreductases of filamentous ascomycetes tested by them, a relationship which is absent with other NADPH cytochrome P450 oxidoreductases, such as those of the yeast *Saccharomyces cerevisiae*.

To date, a limited number of genes coding for cytochrome P450 enzymes from filamentous fungi have been cloned. Further, some biochemical/biotransformation knowledge about a few cytochrome P450 enzymes is available. The genes which have been cloned to date code for a lanosterol 14α-demethylase from *Penicillium italicum* (CYP51), benzoic acid para-hydroxylase from *Aspergillus niger* (CYP53), a cycloheximide inducible cytochrome P450 from *Neurospora crassa* (CYP54), a nitrate/nitrite inducible cytochrome P450 from *Fasarium oxysporum* (CYP55) and pisatin demethylase from *Nectria haematococca* (CYP57). In particular with regard to the first (CYP51) and the last (CYP57) enzyme system, a fair amount of biochemical knowledge is available. The CYP51 enzyme is the point of application for very many fungicides and has therefore been studied from the point of view of use for years. In addition, biochemical knowledge has been published with regard to hydroxylation of biphenyl-like compounds by Aspergillus species.

Heterologous expression of a fungal cytochrome P450 in a non-related fungal host has been described for CYP57. It has been found that the mere transfer of the gene coding for pisatin demethylase from *N. haematococca* to *Aspergillus nidulans* leads to the new host acquiring the ability to demethylate pisatin. This indicates that all other components required for the formation of a functional enzyme complex in *Aspergillus nidulans* were already present and that they are also capable of forming in vivo an active enzyme complex with a heterologous cytochrome P450.

Increasing the production of a specific cytochrome P450 enzyme (for instance through the introduction of additional gene copies coding for this enzyme) definitely does not always ensure an increase of the total activity of this specific enzymatic reaction. In fact, the introduction of several P450 enzymes to increase the enzymatic activity is suitable only to a certain extent. This will appear from a publication (Van Gorcom et al. (1990) Mol. Gen. Genet. 223,192–197) describing the cloning and characterization of the gene coding for the cytochrome P450 enzyme benzoic acid para-hydroxylase from *Aspergillus niger*. This publication also describes an attempt to improve the benzoic acid para-hydroxylase activity of *A. niger*. This was attempted by increasing the production of the cytochrome P450 in question. However, the increase of the production of the benzoic acid para-hydroxylase did not have a positive effect on the benzoic acid para-hydroxylase activity. Apparently, another component of the enzyme complex was limiting. It could be that the P450 enzyme is not supplied with sufficient electrons which are necessary to enable the conversions to be carried out.

As yet, little is known with regard to the manner in which these cytochrome P450 enzymes are supplied with their electrons. The donor in the microsomal systems described here is NADPH, but it has not yet been demonstrated in detail how the transport proceeds. It has been demonstrated biochemically that, as with other eukaryotic microsomal systems, this is probably done by one enzyme: the NADPH cytochrome P450 oxidoreductase. It is proposed that the oxidoreductase could be that limiting factor.

Accordingly, although a number of P450 enzymes for particular filamentous fungi have been described, the corresponding oxidoreductases from those specific fungi were not available up to the time of the present invention.

SUMMARY OF THE INVENTION

According to the invention, the enzymatic activity of P450 enzyme systems in filamentous fungi can be improved by means of a new gene coding for a new oxidoreductase, by means of new oxidoreductase and/or by means of the new microorganisms hereinafter described in detail.

Whenever in the present specification 'polypeptide' or 'protein' is mentioned, these terms are understood to refer inter alia to a polypeptide which is at least partly coded for by a DNA sequence according to the invention. Examples include fragments and/or derivatives of the new oxidoreductase which exhibit the desired activity.

The only thing that could possibly be used up to the time of the invention to improve cytochrome P450 reactions in fungi are cytochrome P450 oxidoreductases from other, non-related organisms such as yeasts, plants, insects and mammals. These are the organisms whose corresponding genes are available. In the endeavor to use homologous systems which are adapted to the host as best as possible, the use of a cytochrome P450 oxidoreductase stemming from fungi is naturally to be preferred.

On the basis of the known P450 cytochrome oxidoreductases from other organisms, it should be possible with standard techniques to pick up, isolate and clone the oxidoreductase from filamentous fungi.

Surprisingly, the current techniques, such as nucleic acid hybridizations and standard PCR (Polymerase Chain Reaction), failed in the present case. As will be described in the examples with the present invention, it has proved to be impossible to find a gene coding for the oxidoreductase of filamentous fungi with probes (single-stranded DNA-pieces which are complementary to conserved sequences in other oxidoreductases) which have been prepared in the conventional manner.

In addition, it has been found that the enzyme normally used for PCR (Taq-DNA-polymerase) is also unsuitable for picking up the gene that codes for an oxidoreductase of a filamentous fungus using the primers selected by us, which are based on conserved domains in other NADPH cytochrome P450 oxidoreductases.

Only through the choice of a very highly degenerated probe in combination with an unconventional polymerase have we succeeded in obtaining the gene according to the invention.

The new gene comprises a sequence as shown in FIG. 1 (SEQ. ID NO:1). The amino acid sequence derived therefrom is shown in FIG. 2 (SEQ ID NO:2).

For different kinds of uses it is interesting to increase the biocatalytic activity of a fungal cell. The enzymatic activity level naturally present is often not high enough for more industrial uses of these enzyme systems, for example the detoxification of chemicals and toxins in waste, soil, water and air (environmental uses), the modification and detoxification of (raw materials for the production of) foodstuffs and cattle feeds and the use of fungi, or enzyme complexes isolated therefrom, for carrying out one or more enzymatic conversions for the purpose of the synthesis of a chemical or pharmaceutical intermediate or end product. It is also conceivable that a particular product can be produced entirely through fermentation of a fungus. If this involves one or more cytochrome P450 enzymes, the production can be improved by a strain with an increased NADPH cytochrome P450 oxidoreductase activity.

Cytochrome P450 enzyme activities are often the velocity-limiting steps in a pathway. The increase of this type of enzyme activities will therefore have a positive effect on the extent and rate of conversion of compounds synthesized or degraded by such pathway. Examples of conversions (partly) catalyzed by cytochrome P450 are the para-hydroxylation of benzoic acid and other aromatics, various hydroxylations of biphenyl-like compounds, the specific hydroxylation, epoxidation and demethylation of aromatic and non-aromatic compounds with a multiring structure (such as PAKs and steroid-like molecules), the terminal hydroxylation of (short and long chain) alkanes and fatty acids, the demethylation of phytoalexins, etc., etc. At present it is assumed that many cytochrome P450 enzymes are yet to be discovered. However, in the case of these as yet unknown enzyme activities, too, the invention described here can contribute to the increase of the activities in question.

The results of the invention disclosed here are not limited exclusively to the organism with which the investigation has been carried out, i.e. Aspergillus. Two important reasons for this can be mentioned. Firstly, the conservation among homologous genes of filamentous fungi is mostly such that genes isolated from Aspergillus can serve as a tool for (simply) obtaining the corresponding genes from other filamentous fungi. In view of the conservation in the family of cytochrome P450 oxidoreductases, it is expected that this will definitely apply to this gene too. Secondly, the cprA gene (the gene coding for the oxidoreductases according to the invention) of *Aspergillus niger* can also be used directly in other filamentous fungi as a supplier of additional NADPH cytochrome P450 oxidoreductase activity. It has been found in the past years that the isolation of genes from fungi through heterologous hybridization with the corresponding gene from yeasts as probes is quite often unsuccessful. In these cases the use of a corresponding gene stemming from a filamentous fungus often did prove successful. Even the isolation of genes through PCR experiments using as primers oligonucleotides designed starting from (possibly) conserved regions in yeast genes did not prove by any means to be always a useful approach.

It has further been found that genes from filamentous fungi can be eminently used for carrying out corresponding tasks in other fungi. The promoters are normally functional and introns, too, unlike in the case of yeast, are correctly spliced by other fungi. Exchange of proteins in fungi forming part of a more complex system, which also holds, for instance, for cytochrome P450 enzyme systems, has already been found to be a real possibility several times. Both a subunit of tubulins and a nucleo-coded subunit of a mitochondrial ATPase complex have been found to be exchangeable between different kinds of filamentous fungi in vivo. In vitro, the exchangeability of NADPH cytochrome P450 oxidoreductase between different filamentous fungi has already been demonstrated.

With regard to the activity of the NADPH cytochrome P450 oxidoreductase, it is conceivable that modifications on the protein (provided in directed or non-directed manner) can lead to an NADPH cytochrome P450 oxidoreductase with better properties in general or for a specific use. This kind of adjustments to the protein (via adjustments in the gene) have become possible through the present invention and therefore fall within the scope of protection.

It is also known, in respect of other organisms, that fusion of a specific cytochrome P450 with the NADPH cytochrome P450 oxidoreductase, to be effected through a fusion of the genes in question, can lead to enzymatically active molecules. In a number of cases, this may even have a positive effect on the total enzymatic activity of the cytochrome P450 in question. Such a fusion is also understood to fall within the scope of the present invention.

It is highly doubtful whether it is possible to eliminate the NADPH cytochrome P450 oxidoreductase activity in the cell. This enzyme is involved in a number of activities which are essential to the cell, so that a mutation (directed or randomly provided) in the genome which leads to the elimination of the NADPH cytochrome P450 oxidoreductase activity is probably lethal. However, it is quite plausible that a change of the expression signals of the gene that codes for NADPH cytochrome P450 oxidoreductase (cprA) can also lead to the desired effect (a change (mostly an increase) in the NADPH cytochrome P450 oxidoreductase activity). The data presently available indicate that the promoter of the *Aspergillus niger* cprA gene is not particularly strong. On the basis of the knowledge becoming available through this invention, the strategy which will lead to an increase in the NADPH cytochrome P450 oxidoreductase activity through modification of the promoter and/or the 5' untranslated part of the cprA gene is simple to specify. It can be effected through modification (directed or random) of its own sequences involved in the initiation of mRNA and protein synthesis of the cprA gene. It can also be effected through replacement of the promoter and/or a part of the region of the cprA gene coding for the 5' untranslated part of the mRNA by other, preferably more efficient, sequences (synthetic or stemming from a different gene).

A totally different use of the gene is the use of this gene, or parts thereof such as the promoter, as a reporter for the detection of inducing agents zoals toxins, xenobiotics and the like. Because of the general character of this enzyme it is quite conceivable that in this manner a 'wide-spectrum' diagnostic can be developed. In this connection one could for instance consider fusion of the expression signals of the gene to a simply detectable reporter gene (coding, for instance, for β-galactosidase, β-glucuronidase or luciferase), or detection methods based on immunological techniques.

Although the in vitro use of cytochrome P450 enzyme systems is not yet employed on a large scale, this invention provides the possibility of producing one of the components of such an in vitro enzyme system (the NADPH cytochrome P450 oxidoreductase) on a large scale. This invention also contemplates the making of fungal strains which produce both the cytochrome P450 in question and the NADPH cytochrome P450 oxidoreductase in increased amounts, so that the enzyme complex can be isolated therefrom in simpler manner and in larger amounts.

BRIEF DESCRIPTION OF THE DRAWINGS

FIG. 1 shows the DNA sequence of SEQ ID NO:1.

FIG. 2 shows the amino acid sequence of SEQ ID NO:2.

DETAILED DESCRIPTION OF THE INVENTION

Experimental

Figure 3:
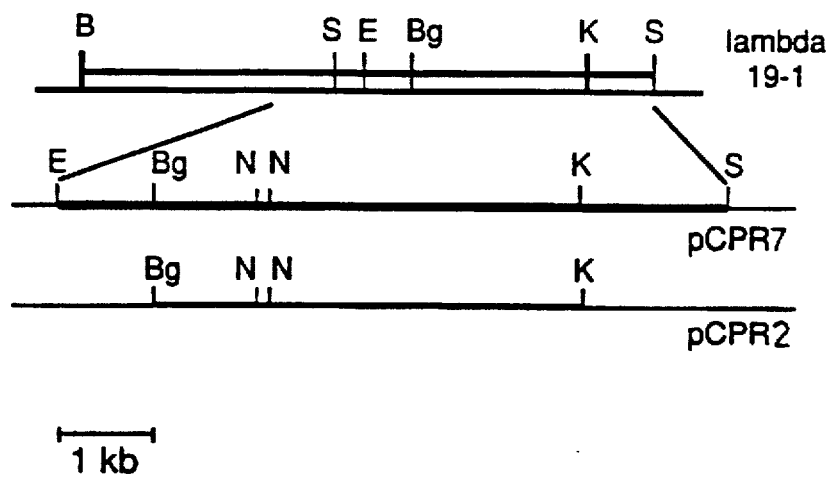
FIG. 3 shows a representation of the picked-up positive λ-clone, λ19-1 and the subclones constructed therefrom, pCPR2 and pCPR7. (S=SalI, E=EcoRi, Bg=BglII, K=KpnI, N=NcoI)

Described herein is the cloning and characterization of a gene which codes for a NADPH cytochrome P450 oxidoreductase or a filamentous fungus.

This involves in particular the cprA gene of *Aspergillus niger* ATCC 1015. Initially, an attempt was made to isolate the gene that codes for NADPH cytochrome P450 oxidoreductase from *Aspergillus niger* through heterologous hybridization. The corresponding genes of the yeasts *Saccharomyces cerevisiae* and *Candida tropicalis* were used as probes. These experiments did not lead to positive results (see Example I).

Then an attempt was made to isolate the gene through PCR. On the basis of a comparison of known protein sequences of NADPH cytochrome P450 oxidoreductases from other organisms, primers were designed which code for amino acid sequences from the most conserved regions. These primers were used in PCR experiments as described in Example II. This PCR gave various bands, but not at the expected heights. Subsequently, after a gel electrophoresis of the PCR mixture, the region of the expected size was excised from gel and the (non-visible) DNA was isolated therefrom. Then a renewed PCR reaction was performed on this DNA with the same primers. This PCR did yield a product of the expected size. This PCR product was isolated and cloned into pUC19. However, DNA sequence analysis of the isolated clone yielded a DNA sequence which did not show any similarity whatever to a known NADPH cytochrome P450 oxidoreductase sequence.

When this attempt proved negative too, an attempt was made to isolate the gene by means of a probe synthesized in an alternative way (Example III). A PCR reaction was performed using *Aspergillus niger* genomic DNA as template and degenerated primers derived from conserved regions from the NADPH cytochrome P450 oxidoreductase. In this experiment, in contrast with the conventional enzyme (Taq DNA polymerase), now a different thermoresistant DNA polymerase was used, viz. the so-called Tth DNA polymerase. This enzyme comes from the bacterium *Thermus thermophylus* and is generally recommended for use in PCR experiments with RNA as template. By means of this enzyme, too, many different bands were found, among others a band of the expected size. This band was isolated and cloned in pUC19. Sequence analysis of a single clone, pCPR1, gave a clearly recognizable similarity (at protein level) to the NADPH cytochrome P450 oxidoreductase sequences known at that time. This clone was used as a probe for the purpose of the isolation of the NADPH cytochrome P450 oxidoreductase gene of *Aspergillus niger* from a gene library.

The *Aspergillus niger* cprA gene was isolated on a 7 kb EcoRI-SalI fragment (pCPR7) and a 3.7 kb BglII-KpnI fragment (Example IV). The DNA sequence of the complete 3.7 kb BglII-KpnI fragment was determined. It is shown in FIG. I (SEQ ID NO: 1). In this DNA sequence an open reading frame was found, coding for 692 amino acids. This open reading frame is interrupted once by a DNA sequence coding for an intron (see Example V). The start of the mRNA was also determined (Example VI).

A comparison of the deduced amino acid sequence with the known amino acid sequences of NADPH cytochrome P450 oxidoreductases from other organisms indicated that the identicality with the NADPH cytochrome P450 oxidoreductase most closely related on the basis of amino acid sequences (that of the yeast *Saccharomyces cerevisiae*) is only 40%. In various "conserved" regions of the *Aspergillus niger* NADPH cytochrome P450 oxidoreductase, too, the identicality is not 100%.

The expression of the *Aspergillus niger* cprA gene on an mRNA level was also analyzed. The expression of the gene is found to be not very high, which provides possibilities for the improvement of the expression by improving the cprA promoter or by replacing the cprA promoter by a different, stronger promoter.

The effect of the introduction of several copies of the *Aspergillus niger* cprA gene on the extent of NADPH cytochrome P450 oxidoreductase activity was studied, as was the effect thereof on the cytochrome P450 activity.

Example XI describes that the introduction of several copies of the cprA gene into *Aspergillus niger* can lead to a strongly increased NADPH cytochrome P450 oxidoreductase activity. The effect of this on the benzoic acid parahydroxylase activity of this strain (wild-type) is also presented in this example.

Example XII describes that the introduction of several copies of the cprA gene into an *Aspergillus niger* transformant which already contains several copies of the benzoic acid parahydroxylase gene (bphA) (and, as a result, has an increased production of the benzoic acid para-hydroxylase) can lead to a very substantial increase of the BPH activity. These experiments clearly show that the NADPH cytochrome P450 oxidoreductase gene described in this patent application, when introduced into a fungus, can have a very positive effect on cytochrome P450 activities.

EXAMPLE I

Cloning of the cprA gene of *Aspergillus niger* by means of hetearologous hybridization Insofar as they are not described in detail, techniques were carried out as described (Sambrook, Fritsch & Maniatis (1989) Moleculair cloning, Cold Spring Harbor Laboratory Press, U.S.A.).

An attempt was made to isolate the gene coding for cytochrome P450 reductase of *Aspergillus niger* ATCC 1015 by means of heterologous hybridization experiments. To that end, chromosomal DNA (5 µg) of *Aspergillus niger* and of *Saccharomyces cerevisiae* was digested with HindIII and with EcoRI. This DNA was separated by means of electrophoresis on a 0.8% TBE-agarose gel and transferred to a Hybond N membrane (Amersham). In this way several identical blots were made. After fixation of the DNA on the membrane by baking for 2 hours at 80° C. and 2–4 hours of prehybridization, the blot was hybridized with a $^{32}$p labeled (Amersham multiprime DNA labeling kit, in accordance with the manufacturer's directions) cytochrome P450 reductase specific probes coming from *Candida tropicalis* and *Saccharomyces cerevisiae*, respectively. As a probe for the *Candida tropicalis* CPR gene, a 820 bp EcoRI fragment containing a part of the cpr1 and a 3.7 kb SpeI fragment comprising the entire CPR gene were isolated from plasmid pTS1 (Sutter et al., 1990, J. Biol. Chem. 265 (27), 16428–16436). As a *Saccharomyces cerevisiae* CPR specific probe, a 700 bp BamHI fragment containing an internal part of the CPR and a 3.3. kb PvuII fragment comprising the entire CPR gene were isolated from plasmid pTS20 (Sutter & Loper, 1989, Bioch. Biophys. Res. Comm. 160(3), 1257–1266). The fragments were separated by electrophoresis on a 0.8% TBE-agarose gel and purified by means of the Geneclean kit (Bio101) in accordance with the supplier's directions. The blots were hybridized and washed at 56° C. as described (Sambrook, Fritsch & Maniatis (1989) Molecular cloning, Cold Spring Harbor Laboratory Press, U.S.A.). The last washing step was performed at 56° C. with 6×SSC, 0.1% SDS. With the *S. cerevisiae* probe, clear, specific hybridizing bands could be seen in the lanes with *S. cerevisiae* chromosomal DNA. Experiments with the *C. tropicalis* probes were exclusively performed on chromosomal DNA of *Aspergillus niger*. Surprisingly, with neither probe hybridizing bands were found in the lanes with *Aspergillus niger* chromosomal DNA, possibly caused by too limited a homology between the *Aspergillus niger* cytochrome P450 reductase gene on the one hand and the *S. cerevisiae* and *C. tropicalis* cytochrome P450 reductase genes on the other.

EXAMPLE II

Cloning of the cprA gene of *Aspergillus niger* by means of PCR with Taq DNA polymerase In view of the negative results in the heterologous hybridization experiments, it was decided to attempt to synthesize a cpr specific fragment by means of the PCR technique. Degenerated primers were resigned, based on conserved sequences in known cytochrome P450 oxidoreductase genes of rat (Porter & Kasper (1985) Proc. Natl. Acad. Sci. U.S.A. 82, 973–977); *Candida tropicalis* (Sutter et al. (1990) J. Biol. Chem. 265, 16428–16436); and *Saccharomyces cerevisiae* (Sutter & Loper (1989) Bioch. Biophys. Res. Comm. 160, 1257–1266) (Table I). At the ends, additional sequences were provided, coding for specific restriction sites (5' PCR primers were provided with an EcoRI restriction site, 3' primers with a BamHI restriction size) to facilitate the cloning of PCR products and to increase the specificity of the procedure.

TABLE I

| | | |
|---|---|---|
| MBL 997 | EcoRI<br>5'- CCG GAA TTC CA(G/A) ACN GGN ACN GCN GA(G/A) GA - 3'(SEQ ID NO:3) | |
| | degenerated 1024 times, FMN binding site | |
| MBL 998 | EcoRI<br>5' - CCG GAA TTC GGN GAN CCN ACN GA(C/T) AA(C/T) GC - 3'(SEQ. ID NO:4) | |
| | degenerated 1024 times, FMN binding site | |
| MBL 999 | BamHI<br>5' - CGC GGA TCC GGN CCN A (C/T)N A(G/T/A) (G/T/A) ATN AC - 3'(SEQ. ID NO:5) | |
| | degenerated 4608 times, NADPH binding site | |
| MBL 1000 | BamHI<br>5' - GCG GGA TCC T(C/G) (C/T) TGN AC(G/A) TAN AC(C/T) TT - 3'(SEQ ID NO: 6) | |
| | degernated 256 times, NADPH binding site | |
| MBL 1001 | BamHI<br>5' - CGC GGA TCC GGN CC(G/T/A) ATC AT(G/T/A) ATN AC - 3'(SEQ ID NO:7) | |
| | degenerated 144 times, NADPH binding site | |

Table I, sequences of the primers used for the isolation of a cpr specific probe. N stands for G/A/T/C.

For the PCR reactions, Taq DNA polymerase (Perkin Elmer) was used. As template, *Aspergillus niger* chromosomal DNA was used. By way of check, PCR reactions were performed using as template 10 ng of the plasmid pTS20 (on which is located the entire cytochrome P450 reductase gene of *Saccharomyces cerevisiae*) and chromosomal DNA of *Saccharomyces cerevisiae*.

Template and primers were denatured for 10 minutes at 94° C., followed by 25 cycli (1 minute 94° C., 1 minute 43° C., 2 minutes 72° C.). After 25 cycli, incubation took place for 5 minutes at 72° C.

When Taq DNA polymerase with plasmid pTS20 as template was used, fragments of the expected size were found when primer combinations MBL997-MBL999, MBL997-MBL1000 and MBL997-MBL1001 were used. The use of primer MBL998 did not in any of the cases lead to synthesis of a product of the expected size.

The use of *S. cerevisiae* chromosomal DNA as template led to a clearly demonstrable product of the expected size when the primer combination MBL997-MBL1001 was used. The use of the combination of MBL997 with the primer MBL999, degenerated 4608 times, led to a weakly demonstrable product of the expected size. In all of these cases a large amount of a specific product of smaller sizes was found. With the primers MBL998 and MBL1000, using *S. cerevisiae* chromosomal DNA as template, no correct PCR product could be demonstrated.

When *Aspergillus niger* chromosomal DNA was used as template, and using Taq DNA polymerase, no product of the expected size was found with any of the primer combinations used. What could be demonstrated in all possible combinations was a large amount of a specific, too small, product.

The total material of a single experiment with the primer combinations MBL997-999, MBL997-1000 and MBL997-1001 was separated through electrophoresis on a 0.8% TBE-agarose gel. A piece of gel at the level of a marker band of 1.2 kb (the expected size) was excised. At this location in the gel no DNA was visible. DNA from this gel fragment was isolated by means of the freeze squeeze method. The so obtained material was used as template for a new PCR reaction. Surprisingly, after this reaction a product of the expected size was found when using the primer combinations MBL998/999 and MBL998/1001. However, with all of the primer combinations used (MBL997-MBL999,1000,1001 and MBL998-MBL999, 1000,1001) mainly smaller, a specific, products were found. The product of the expected size that was found was separated through gel electrophoresis on a 0.8% Low Melting Point agarose gel whereafter DNA was isolated by means of β-agarase (New England Biolabs, in accordance with the directions of the supplier). The DNA obtained was digested with EcoRI and BamHI and cloned into the EcoRI and BamHI sites of pUC19. After transformation to *Escherichia coli*, miniscreen DNA was isolated from 12 ampicillin resistant colonies. After digestion of the obtained miniscreen DNA with EcoRI and BamHI, only one construct was found to contain an insert of the correct size. Of this a large plasmid isolation was done, using a Qiagen Tip500 in accordance with the supplier's instructions. The DNA sequence of this construct was analyzed by dideoxy sequence analysis (Pharmacia T7 sequencing kit, according to the supplier's instructions) using the M13 universal and reverse primer. In the DNA sequence as determined, no homology with known cytochrome P450 reductase genes of other organisms was found.

EXAMPLE III

Cloning of the cprA gene of *Aspergillus niger* by means of PCR with Tth DNA polymerase As an alternative, it was decided to perform PCR experiments using, instead of 1 unit Taq DNA polymerase, 0.1 unit Tth DNA polymerase (Spaero Q), an enzyme which is particularly suitable for RT-PCR (reverse transcriptase PCR) experiments. Using plasmid pTS20 as template, this resulted in products of the expected size when using primer combinations MBL997–999, MBL997–1000 and MBL997–1001. When *Aspergillus niger* chromosomal DNA was used as template, this resulted in a large amount of products when using primer combination MBL997–1001. The majority of these products were found to be smaller than the expected size. Surprisingly, when using these degenerated primers in combination with Tth DNA Polymerase, in addition to the a specific products, a product of the expected size was found. The PCR products were separated by means of gel electrophoresis on a 1% TBE-low melting point agarose gel, whereafter the presumably correct product was isolated by means of β-agarase.

After digestion of the obtained DNA with EcoRI and BamHI, the fragment was cloned into the EcoRI and BamHI restriction sites of plasmid pUC19. After transformation to *E. coli*, miniscreen DNA was isolated from 12 ampicillin resistant colonies. After digestion of the miniscreen DNA with EcoRI and BamHI, 4 of the 12 preparations were found to contain a plasmid with an insert of the correct size.

Of these four preparations, of one construct (pCPR1) a large DNA isolation was done by means of a Qiagen Tip500. Of this DNA, the sequence of a part of the insert was determined by means of the M13 universal and reversed primer. This sequence was found to contain regions which, at an amino acid level, were clearly homologous to other cytochrome P450 reductase genes.

EXAMPLE IV

Screening of *Aspergillus niger* λ-gene library with the cpr specific probe

Figure 4:
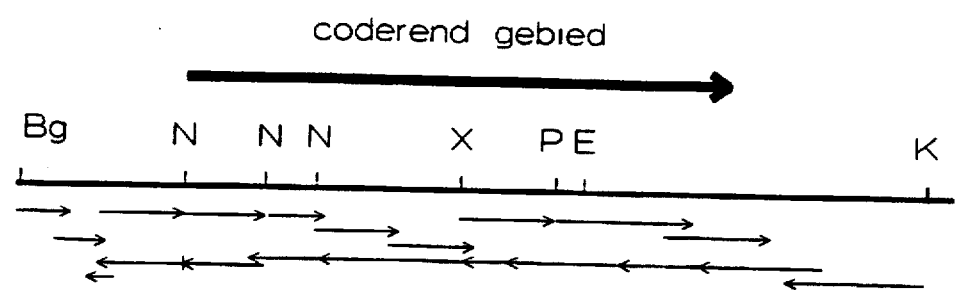
FIG. 4 shows a representation of the insert of pCPR2, on which the CPR gene is located. The regions whose sequence has been determined are indicated by arrows. (Bg=BglII, K=KpnI, N=NcoI, X=XhoI, P=PstI)

Genomic DNA of the *Aspergillus niger* strain ATCC 1015 was partially digested with Sau3AI and separated by gel electrophoresis. DNA of between 13 and 17 kb in size was isolated from the gel and the DNA was isolated. The isolated DNA was cloned into vector λEMBL3, digested with BamHI. This genomic library was screened with the cpr specific probe isolated from plasmid pCPR1 (the 1.2 kb EcoRI-BamHI fragment, see FIG. 4). The isolated EcoRI-BamHI restriction fragment, with the cpr specific PCR fragment, was radioactively labeled with $^{32}$P-dCTP using the multiprime DNA labeling kit. (Amersham) in accordance with the supplier's instructions. Labeling reactions were performed for 3 hours at room temperature. The probe was purified by spin column filtration over a 1 ml Sephadex G50-medium column. About 40,000 pfu were screened (about 20 times the genome). In the first screening 13 positive plaques were isolated. These were screened again. After the second screening, 3 positive plaques remained (λ5-3, λ11-1 and λ19-1). Through Southern analysis it was demonstrated that all clones contained fragments which hybridized with the cpr specific probe. The restriction patterns of these clones were clearly related but not identical. A restriction map of clone λ19-1 was made (see FIG. 3). A 7 kb EcoRI-SalI fragment and a 3.7 kb BglII-KpnI fragment of clone λ19-1, which contain the coding region of the cprA gene, were isolated and cloned into vector pBluescript-SK II⁺ (Stratagene) digested, respectively, with EcoRI and SalI and with BamHI and KpnI. This resulted in the vectors pCPR7 and pCPR2 (see FIGS. 3 and 4).

EXAMPLE V

Sequence analysis of the *Aspergillus niger* cprA gene

The sequence of both strands of the *Aspergillus niger* BglII-KpnI fragment cloned into plasmid pPCPR2 was determined according to the "dideoxy chain terminating" method (Sanger et al. (1977) Proc. Natl. Acad. Sci. U.S.A. 74, 5463–5467) using the $^{35}$S-dATP T7 DNA sequencing kit (Pharmacia) in accordance with the supplier's instructions. Sequence analysis of subclones was performed using the M13 universal and reverse primers. Parts of the sequence were determined using synthetic oligonucleotides, using pCPR2 ds-DNA as template (see FIG. 4). Sequence information was analyzed with GCG software (Devereux et al., (1984) Nucleic Acids Res 12, 387–395).

In the DNA sequence a region possibly coding for an intron was found (FIG. 2, position 2367 . . . 2437). The actual absence of this intron in the mRNA of the cprA gene was demonstrated with RT-PCR experiments. In them the expected difference in size of the PCR product was found when using primers located around the intron, with chromosomal DNA or isolated total RNA as template (GeneAmp RNA-PCR kit, Perkin Elmer).

The deduced amino acid sequence of the *Aspergillus niger* cprA gene was found to show a 39–46% identicality to the amino acid sequences of the CPRs of the yeasts *Saccharomyces cerevisiae*, *Candida tropicalis* and *Schizosaccharomyces pombe* and the genes from rodents and an approximate 35% identicality to the CPR amino acid sequences of plants published to date.

EXAMPLE VI

Determination of transcription start

For determining the transcription start of the *Aspergillus niger* cytochrome P450 reductase gene, a primer extension experiment was performed. To that end, two primers, PE50 and PE100, were designed. These primers were based on sequences located on, respectively, 50 bp and 100 bp 3' of the ATG and read in the direction of the ATG.

PE50
5' CCA-CGC-TAC-CCA-C 3' (SEQ ID NO:8)
PE100
5' GAG-GCA-TAC-GGG-TC 3' (SEQ ID NO:9)

RNA was isolated from *Aspergillus niger* transformant T16 (van Gorcom et al., (1990) Mol Gen Genet 223, 192–197). Mycelium was cultured and ground in liquid nitrogen. The fine powder was resuspended in 1 ml RNAzol (Cinna/Biotecx) whereafter the isolation was continued in accordance with the supplier's instructions.

Of both primers 100 ng was kinated with 5 μl $^{32}$P-yATP. Reactions were performed for 30 minutes at 37° C. as described (Sambrook, Fritsch & Maniatis (1989) Molecular cloning, Cold Spring Harbor Laboratory Press, U.S.A.). After the incubation the primers were purified by filtration over a Sephadex G50 spin column. Added to this primer was NH$_4$ acetate to a final concentration of 2M and 2.5 volume ice-cold Ethanol. Primers were precipitated at −20° C. for 60 minutes. Primers were pelletized by centrifugation at 4° C., 14000 rpm. for 30 minutes, whereafter the pellets were washed with 70% ethanol and were resuspended in 20 μl TE.

Primers were ex-ended with M-MLV reverse transcriptase for 1 hour at 37° C. The reaction mix (25 μl) contained 10 μg RNA, 50 mM NaCl, 34 mM Tris-HCl/pH 8.3, 6 mM MgCl$_2$, 5 mM DTT, 200 U M-MLV reverse transcriptase (Gibco), 0.5 mM dGTP, 0.5 mM dATP, 0.5 mM dCTP, 0.5 mM dTTP and 5 μl (25 ng) of the kinated primer.

The reactions were stopped by the addition of 2 μl 0.5M EDTA, followed by an alcohol precipitation (60 minutes −20° C.). After centrifugation (30 minutes, 14000 rpm, 4° C.) the pellet was resuspended in 5 μl distilled water. To the mix was added 3.4 μl stop mix (Pharmacia T7 polymerase sequencing kit). Before being applied to gel, the samples were denatured by incubation at 95° C. for 5 minutes, whereafter they were directly placed on ice. One half of the sample was applied to a 8% wedge shape denaturing polyacrylamid gel.

By way of check, sequence reactions were performed with both primers (Pharmacia T7 polymerase sequencing kit) with plasmid pCPR2 as template and applied to gel simultaneously with the primer extension mix. After 2 hours of electrophoresis (1100 V) the gel was dried and an X-ray sensitive film was exposed.

Strikingly, results with primer PE50 were much stronger than with primer PE100. In particular in the lanes with primer PE50 a great many bands were visible. Combination of both results led to the designation of three possible transcription start positions, viz. at 86 bp (ctcActc), 55 bp (cagActcg) and 37 bp (aagTcgg) before the ATG. The last band was not found when primer PE100 was used.

EXAMPLE VII
Transformation of *Aspergillus niger* strains

The *Aspergillus niger* strains N204 (ATCC 1015, csp, met, Boschloo et al., Appl Microbiol Biotechnol (1990) 34, 225–228; contains 1 copy of the bphA gene) and T18 (*Aspergillus niger* N271 provided with about 12 copies of the bphA gene; van Gorcom et al. (1990) Mol Gen Genet 223, 192–197) were cultured in 250 ml complete medium (minimal medium supplemented with 0.1% Cas amino acids, 0.5% Yeast extract, 0.1 mg/ml methionine, 1 µg/ml pyridoxine) in 2l Erlenmeyer flasks. The cultures were inoculated with $1.10^6$ spores per ml and then incubated for 18 hours in an air-agitated incubator at 35° C. and 300 rpm. After incubation, mycelium was harvested by filtration through a miracloth filter (Calbiochem). This mycelium was then protoplasted and the protoplasts isolated therefrom were transformed as described by Yelton et al., Proc. Natl. Aca. Sci. USA 81 (1984) 1470–1474.

Samples of 100 µl protoplasts were transformed with, in all, 1 µg circular pAN7-1 DNA, 9 µg circular pCPR2 DNA, and 2 µl of a 1M ATA (Aureen tri-carboxyl acid) solution. Control tubes contained no DNA or only 1 µg pAN7-1 (Punt et al., Gene 56 (1987) 117–124). The transformed protoplasts were then plated on minimal medium agar plates supplemented with 1.2M sorbitol, 1 µg/ml pyridoxine, 0.1 mg/ml methionine and 100 µg/ml hygromycin. The plates were incubated for 10 days at 35° C. After 4 days the first sporulating transformants became visible. Transformants were twice applied with a brush to form pure cultures on minimal medium agar plates with 100 µg/ml hygromycin, 0.1 mg/ml methionine and 1 µg/ml pyridoxine.

Per transformation 10 to 40 hygromycin resistant transformants could be formed. On transformation plates of protoplasts which had been treated without DNA, no hygromycin resistant transformants could be found after 14 days of incubation at 35° C.

EXAMPLE VIII
Screening of transformants
T18 multiple copy cprA transformants

The transformants from Example VII were tested for their hygromycin resistance level by plating of spores on minimal medium agar plates supplemented with 500 µg/ml hygromycin, 0.1 mg/ml methionine and 1 µg/ml pyridoxine.

For selecting transformants with an increased cprA mRNA level, an RNA colony hybridization experiment was performed according to a modified version of the protocol as was described for *Saccharomyces cerevisiae* by Stepien and Butow (1992, Nucl.Acids Res. 18(2) p380). Minimal medium agar plates were inoculated with spores of transformants, covered with a Hybond-N filter, and subsequently incubated at 25° C. until mycelium was just visible but spore formation had not developed yet. The filters were transferred to a 500 µl drop of sorbitol buffer (1.2M sorbitol, 0.1M sodium citrate/pH 5.8, 0.1M EDTA, 50 mM µ-mercapto-ethanol), incubated for 5 minutes and subsequently transferred to a sheet of Whatmann 3 MM filtering paper. After drying for 5 minutes on the Whatmann paper, the filters were transferred to a Petri dish with a drop (500 µl) of sorbitol buffer to which 10 mg/ml Novozym 234 (NOVO Nordisk) had been added. The Petri dish was closed airtightly with parafilm and the mycelium was protoplasted for 1 hour by incubation at 35° C. After protoplasting, the protoplasts were lysed by transferring the filter to a 500 µl drop of lysis buffer (2% SDS, 7.3% formaldehyde, 50 mM Tris-HCl/pH 7.5, 10 mM EDTA) followed by an incubation of 5 minutes at room temperature. The RNA was blotted on the filter by transferring the filter, with lysed protoplasts, to a sheet of Whatmann 3 MM filtering paper until the filter was dry (about 5 minutes). This blotting step was repeated a single time. Finally, the filters were transferred for 1 minute to a drop of 800 µl 6×SSC (Sambrook et al, ***), 0.1% SDS and subsequently dried by transferring the filter to a sheet of Whatmann 3 MM paper. The RNA was fixed on the Hybond N filter through UV crosslinking. To that end, the filter was set on a UV light box for 3 minutes. The filters were hybridized overnight at 65° C. with a $^{32}$p-dCTP labeled cprA probe. The filters were washed at 65° C., utilizing 0.2×SSC, 0.1% SDS in the last washing step. After overnight exposure at –70° C., positive transformants could be identified.

N204 multiple copy cprA transformants

Hygromycin resistant transformants of N204 were screened with an RNA colony hybridization in which a cprA specific probe was used. A second screening was performed with a cytochrome P450 reductase specific filter activity assay. For this purpose, spores of hygromycin resistant transformants were inoculated on minimal medium agar plates supplemented with 0.1 mg/ml methionine and 1 µg/ml pyridoxine. The plates were covered with a Hybond N filter and incubated at 25° C. until mycelium was just visible but virtually no spores had been formed yet. The filters were removed, the mycelium was lysed by freezing in liquid nitrogen and subsequent defrosting. The filter was incubated in the dark for about one hour in 25 ml neotetrazolium solution (5 mg Neotetrazolium, 5 mg NADPH per 25 ml). At locations with cytochrome P450 reductase activity, a clearly pink precipitate is formed.

On the basis of the two screening methods, transformants W13 and W35 were selected as presumable multiple copy cprA transformants.

EXAMPLE IX
DNA analysis of transformants

Mycelium of transformants selected in Example VIII was cultured in 50 ml minimal medium, supplemented with 1 µg/ml pyridoxine, 0.1 mg/ml methionine and 0.1% CAS amino acids. Erlenmeyer flasks (300 ml) were inoculated with $1.10^8$ spores and placed in an air-agitated incubator (35° C., 300 rpm). The mycelium was harvested by filtration over miracloth filter (Calbiochem) and washed with 25 ml 0.9% NaCl. The mycelium was immediately frozen in liquid nitrogen. From this mycelium, chromosomal DNA was isolated according to the method described by Kolar et al. (Gene 62 (1988) 127–134). The pellet of the last alcohol precipitation was incorporated in 100 µl distilled water.

Chromosomal DNA (40 µl) was digested with 20 U EcoRI and 20 U KpnI for 6 hours at 37° C. After the digestion equal amounts of DNA were separated on a 0.8% TBE-agarose gel by means of electrophoresis (18 hours, 35 volts). After separation the DNA was transferred to a sheet of Hybond N filter (Amersham) in accordance with the instructions of the supplier. After fixation of the DNA (2 hours, 80° C.) the blot was prehybridized at 65° C. for 4 hours and subsequently hybridized at 65° C. with a $^{32}$p labeled cprA specific probe. The blot was washed at 65° C., the last washing step involving 0.2×SSC, 0.1% SDS. An X-ray sensitive film was exposed at −70° C. For 24 hours.

Seven selected transformants were analyzed in this manner. In one transformant, only the wild-type band was found, in four transformants integration of 1–2 copies of the cprA gene was found and in two transformants integration of several copies of the cprA was found. Of these multiple copy integrants, transformant T18 #5 was selected.

EXAMPLE X

NADPH: Cytochrome P450 (cytochrome c) reductase activity

CPR activity was determined by measuring the possibility of cell free extracts of transformants to reduce cytochrome c. (Adapted from Madyastha et al. (1976) Biochemistry 15, 1097–1102).

Mycelium was cultured for 13 hours in 50 ml minimal medium, supplemented with 0.1% CAS amino acids, 0.1 mg/ml methionine and 0.1 µg/ml pyridoxine. The medium was inoculated with $1.10^6$ spores per ml in 300 ml Erlenmeyer flasks in an air-agitated incubator (35° C., 300 rpm). The mycelium was harvested by filtration over miracloth filter (Calbiochem) and washed with 25 ml 0.9% NaCl. Excess buffer was removed by blotting the filter with mycelium between tissues. The mycelium was frozen in liquid nitrogen and ground in a mortar. The fine powder was transferred to an Eppendorf reaction vessel filled with 1 ml ice-cold CPR-extraction buffer (50 mm sodium phosphate buffer/pH 7.8, 20% glycerol, 1 mM EDTA, 1 mM DTT, 5 µg/ml Leupeptin, 4 mM PMSF, 0.2% sodium deoxycholate). The vessels were directly mixed and placed on ice. The extract was incubated on ice for 15 minutes (solubilization step) and centrifuged for 15 minutes at 4° C., 1000 g. The supernatant was transferred to a new vessel and preserves an ice. Cytochrome c reductase activity was measured directly.

To 1 ml CPR-assay mix (0.3M K-phoschate buffer/pH 7.7, 0.1 mM EDTA, 1 mM KCN) was added 2 µl 20 mM cytochrome C. At room temperature (20°–25° C.) 5–20 µl cell free extract was added and incubated for 1–2 minutes. Reactions were initiated by addition of 1 µl 100 mM NADPH. Reduction of cytochrome c was monitored spectrophotometrically for 3 minutes (550 nm).

Protein concentrations were determined with the Bio Rad protein assay kit in accordance with the instructions of the supplier, using BSA as standard.

Table II, Cytochrome C reductase activities (e=21 mM.cm$^{-1}$) of different strains/transformants.

Values coming from two independent cultures are specified. Percentages are based on the average of the duplo experiments. One unit is the amount of cytochrome C (mM) which is reduced per minute per mg total protein.

| Strain/ transformant | Estimated cprA copy number | Units | Percentage |
|---|---|---|---|
| N204 | 1 | 2.14 | 100 |
| W13 | ≧6 | 20.56 | 960 |
| W35 | ≧6 | 8.12 | 379 |
| T18 | 1 | 2.50 | 117 |
| T18 #5 | ≧10 | 54.57 | 2.550 |

EXAMPLE XI

BPH activity in vitro assay

For measuring BPH activity in vitro a not yet optimized assay was used, based on the benzoate dependent consumption of NADPH by the NADPH cytochrome P450 oxidoreductase.

The BPH activity was measured in vitro in Aspergillus niger strains T18 (1 copy cprA, 12 copies bphA), strain T18 #5 (6 copies cprA, 12 copies bphA), strain N204 (1 copy cprA, 1 copy bphA) and strain W35 (1 copy bphA, multiple copy cprA)

Mycelium was cultured for 18 hours in 250 ml minimal medium, supplemented with 0.1% CAS amino acids, 0.1 mg/ml methionine and 0.1 µg/ml pyridoxine. The medium was inoculated with $1.10^6$ spores per ml in 2 l Erlenmeyer flasks in an air-agitated incubator (35° C., 300 rpm). The mycelium was harvested by filtration over miracloth filter (Calbiochem) and washed with 250 ml 0.9% NaCl. The mycelium was transferred to 2 l Erlenmeyer flasks filled with 250 ml induction medium (minimal medium with pyridoxine and methionine in which, instead of glucose, 0.1% benzoate was present as C-source). Mycelium was harvested by filtration over miracloth filtration cloth. After washing with 0.9% NaCl, excess buffer was removed by blotting the filter with mycelium between tissues. The mycelium was frozen in liquid nitrogen and ground in a mortar. The fine powder was transferred to an Eppendorf reaction vessel filled with 1 ml ice-cold CPR-extraction buffer (50 mM sodium phosphate buffer/pH 7.8, 20% glycerol, 1 mM EDTA, 1 mM DTT, 5 µg/ml Leupeptin, 4 mM PMSF, 0.2% sodium deoxocholate). The vessels were directly mixed and placed on ice. The extract was incubated on ice for 15 minutes (solubilization) and then centrifuged for 15 minutes at 4° C., 3500 rpm. The supernatant was transferred to a new vessel and preserved on ice.

BPH activity was measured by spectrophotometrically monitoring (340 nm) the BPH specific consumption of NADPH by the cytochrome P450 reductase. Cell free extract (10 µl) was added to 500 µl BPH assay buffer (100 mM Tris/pH 7.8, 10 nM MgCl$_2$, 200 µM NADPH). The non-specific NADPH consumption was measured for 2 minutes (δ-BA). Benzoate was added (20 µl of a 20 mM solution) and the NADPH consumption was measured for 4 minutes (δ-BA). BPH specific MADPH consumption was determined by the following calculation method:

$$\frac{(\delta + BA)}{min.} - \frac{(\delta - BA)}{min.} = \delta BA$$

Units (1 unit=1 µmol NADPH consumed per minute per mg total protein) were calculated by multiplying δBA with the extinction coefficient (e=6.22.10$^{-3}$M$^{-1}$cm$^{-1}$).

Protein concentrations were determined with the Bio Rad protein assay kit in accordance with the instructions of the supplier, and BSA was used as standard.

Table IV, in vitro BPH activity. One unit corresponds with the benzoate dependent consumption of NADPH (µM) per minute per mg total protein.

| Strain/ Transformant | Estimated bphA copy number | Estimated cprA copy number | Units | Percentage |
|---|---|---|---|---|
| N204 | 1 | 1 | 365 | 100 |
| W13 | 1 | ≧6 | 577 | 158 |
| T18 | 12 | 1 | 899 | 246 |
| T18 #5 | 12 | ≧10 | 1590 | 435 |

EXAMPLE XII

Bph activity, in vivo HPLC assay

Mycelium was cultured for 18 hours in 500 ml minimal medium, supplemented with 0.1% CAS amino acids, 0.1 mg/ml methionine and 0.1 µg/ml pyridoxine. The medium was inoculated with $1.10^6$ spores per ml in 2 l Erlenmeyer flasks in an air-agitated incubator (35° C., 300 rpm). The mycelium was harvested by filtration over miracloth filter (Calbiochem) and washed with 25 ml 0.9% NaCl. Mycelium was subcultured in induction medium (minimal medium supplemented with 0.1 mg/ml methionine and 0.1 µg/ml pyridoxine, while adding, instead of 1% glucose, 0.1% benzoate as C-source). Samples of the medium were taken after 5 hours.

Samples of 2 µl were analyzed by means of HPLC chromatography an a reversed phase C-18 column (Superchem LC 18-DB) at 30° C., using 10 mM sodium citrate buffer/pH 3, 60% methanol as elution buffer. A flow rate of 1 ml/min. was used. Both benzoate and 4-hydroxybenzoate were detected at 245 nm. Reference samples contained 10 µl 1 mM benzoate and 10 µl 1 mM 4-hydroxybenzoate.

Table IV, concentrations of benzoate and 4-hydroxybenzoate after incubation of transformants for 5 hrs in induction medium. Detection by means of HPLC. *Aspergillus niger* can use 4-hydroxy-benzoate as C-source and so metabolize further. As a result, the sums of the last two columns of the amounts of benzoate and 4-OH-benzoate are not identical.

| Strain/ Transformant | Estimated bpha copy number | Estimated cprA copy number | Benzoate (mM) | 4-OH-Benzoate (mM) |
|---|---|---|---|---|
| medium | — | — | 6.70 | 0.00 |
| N 204 | 1 | 1 | 1.15 | 3.20 |
| W35 | 1 | ≧6 | 0.60 | 3.63 |
| T18 | 12 | 1 | 2.40 | 3.30 |
| T18 #5 | 12 | ≧10 | 0.0056 | 3.28 |

EXAMPLE XIII

To verify the broad action of the cytochrome P450 oxidoreductase gene, experiments were performed in which the effect of CPR overproduction on the activity of a different (in this example even heterologous) cytochrome P450 enzyme was tested.

For that purpose, *Aspergillus niger* strains were constructed which were provided with several copies of the cprA gene of *Aspergillus niger* together with several copies of the gene coding for lanosterol 14α-demethylase (14 dm) from the filamentous fungus *Penicillium italicum*.

Construction of plasmids

Figure 5:
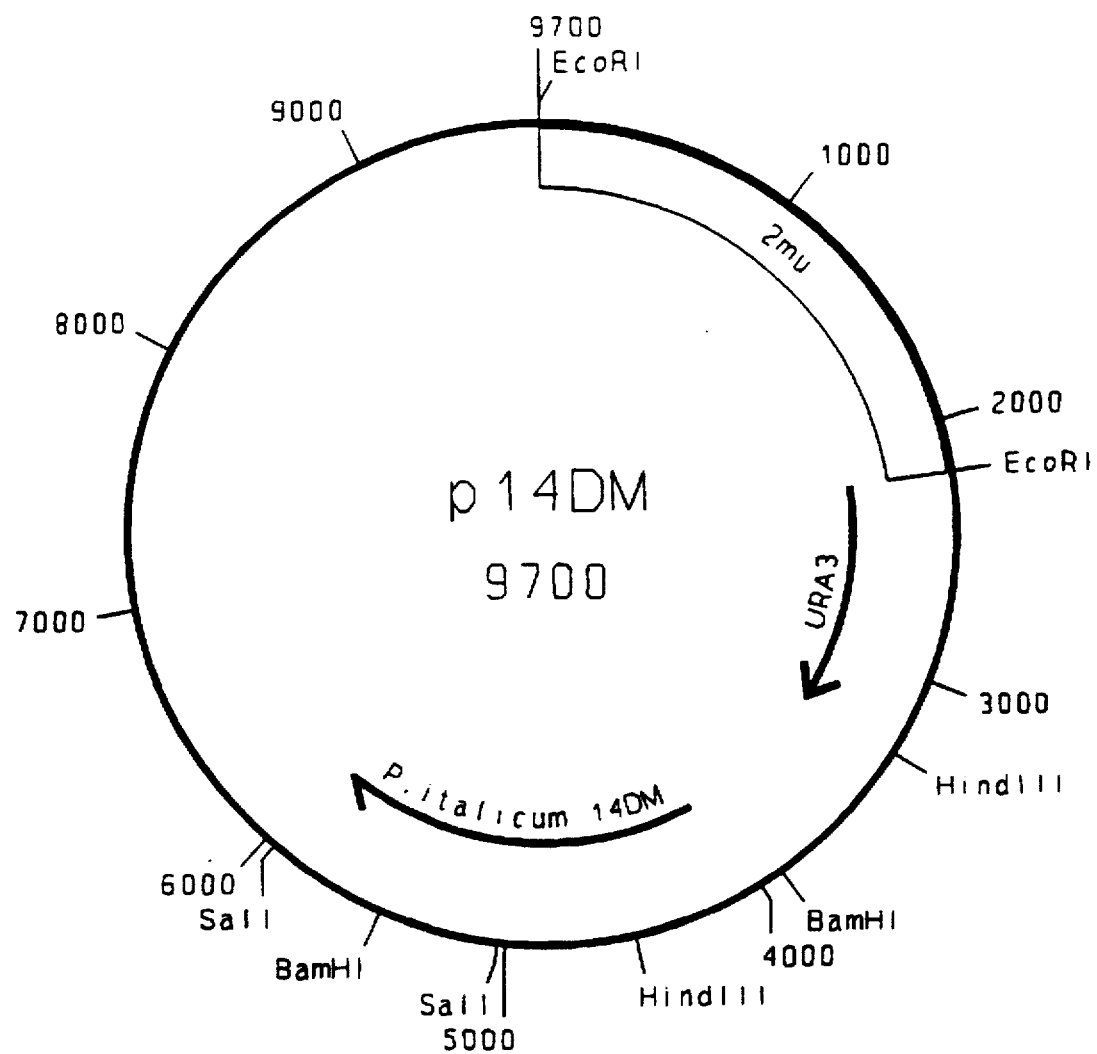
FIG. 5 is a representation of the 14 dm gene from *Penicillium italicum*.

For the introduction of the two genes, two plasmids were constructed. Plasmid pCPR2-amdS was constructed by digesting plasmid pCPR2 with NotI and providing it with a functional copy of the amdS gene of *Aspergillus nidulans* (Hynes et al. Mol. Cell. Biol. 3 (1983) 1430–1439), located on a NotI fragment approximately 5 kb in length (the original ends of the chromosomal amdS fragment (EcoRI and SalI) had been replaced with NotI sites). The amdS gene was used as selection marker in transformation experiments. Plasmid p14 dm was constructed as follows. The yeast-expression plasmid YEP24 was digested with BamHI and SalI. Between these sites was ligated an approximately 2.1 kb chromosomal (partial) BamHI-(partial) SalI fragment, on which the entire 14 dm gene from *Penicillium italicum* was located (see FIG. 5).

Transformation of *Aspergillus niger* pCPR2-amdS

*A. niger* N402 (Bos, PhD Thesis Agricultural University Wageningen NL, 1986) was used as starting strain. Transformation experiments were carried out as described in (Kelly and Hynes EMBO J. 4 (1985) 475–479). *A. niger* N402 was transformed with pCPR2-amdS. Transformants, after being applied with a brush to form pure cultures on selection plates (minimal medium plates with 15 mM CsCl with Acetamide (10 mM) functioning as sole N-source), were further selected for their possibility to use acrylamid as sole N-source. Strains with a high amdS copy number grow better on acrylamid than do strains with a lower copy number (Verdoes et al., Transgenic Research 2 (1993) 84–92).

A selected number of transformants were further analyzed by means of Southern blot analysis. Eventually, transformant AB2-2 (≧10 copies cprA) was selected for further experiments. p14 dm Plasmid p14 dm was introduced into *Aspergillus niger* by means of cotransformation with plasmid pAN7-1 on which the hph gene is located, which affords resistance to Hygromycin (Punt et al. Gene 56 (1987) 117–124). Transformants were selected on plates with 100 µg/ml hygromycin. Positive transformants were thereafter selected for their resistance to higher concentrations of hygromycin. Transformants that grow well at higher concentrations of hygromycin too, were further analyzed by means of Southern Blot analysis. Eventually transformant AB-D1 (≧10 copies 14 dm) was selected for further experiments.

In transformant AB-D1, in a second transformation experiment, an attempt was made to introduce, in addition to extra 14 dm copies, extra cprA copies. Transformant AB-D1 was for this purpose transformed with plasmid pCPR2-amdS. The further selection procedure was identical to the procedure followed for the isolation of transformant AB2-2. Eventually transformant ABD1.15 (≧10 copies 14 dm, ≧10 copies cprA) was selected for further experiments.

| | Cytochrome P450 reductase activity | | |
|---|---|---|---|
| Strain/ Transformant | Estimated 14DM copy number | Estimated cprA copy number | Units |
| N402 | "1" | 1 | 1.05 |
| AB2-2 | "1" | ≧10 | 14.6 |
| AB-D1 | "1" + ≧10 | 1 | 1.65 |
| AB-D1.15 | "1" + ≧10 | ≧10 | 41.7 |

Table V. CPR activity in selected transformants, measured as NADPH dependent cytochrome C reduction and expressed in Units (mmol cytochrome c reduced per minute per mg. total protein). Estimated 14 DM copy number: "1" wildtype *A. niger* 14 DM gene, +: extra copies of the *P. italicum* 14 DM gene. Lanosterol 14α-demethylase activity.

Figure 6:
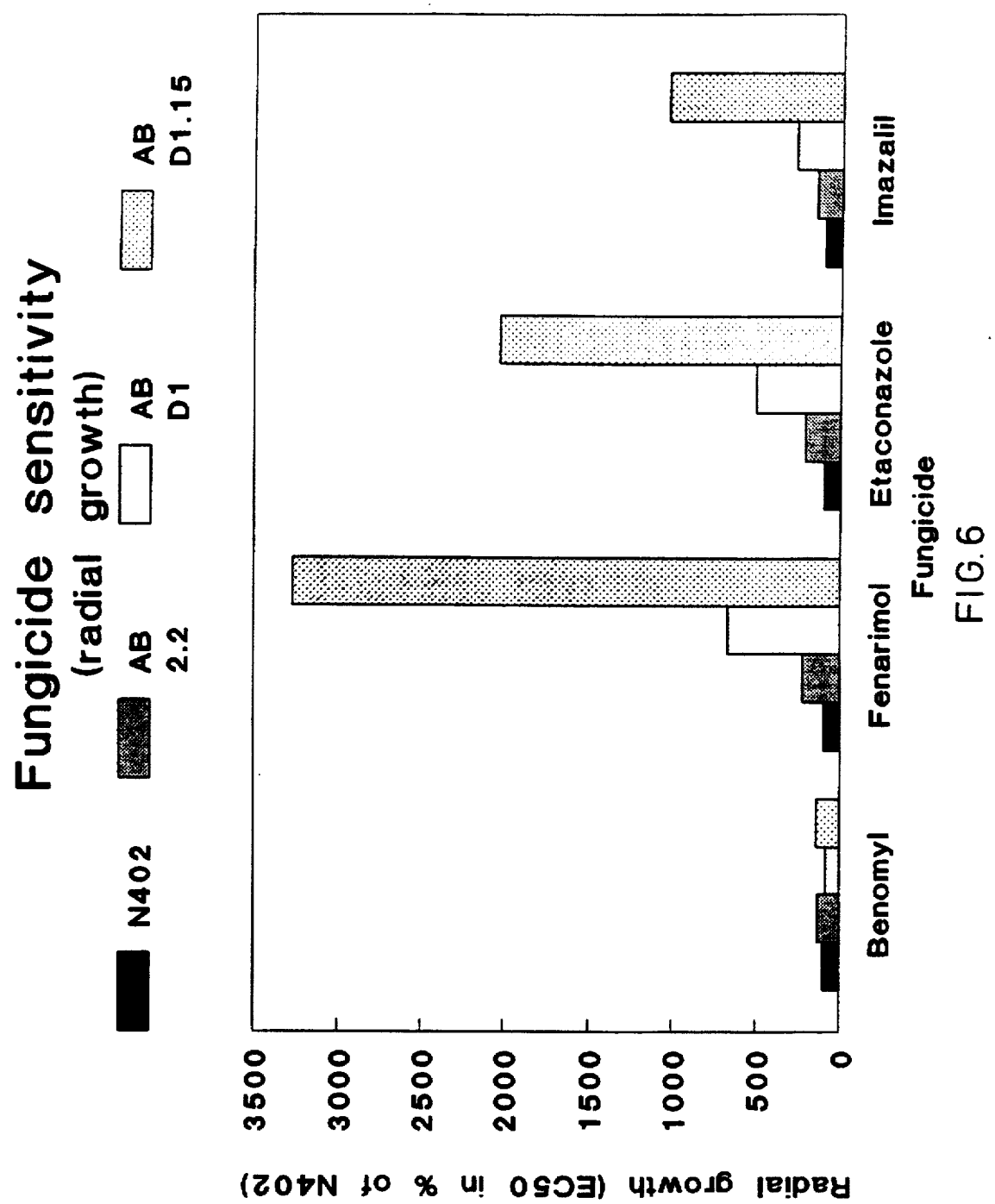
FIG. 6 is a graph showing fungicide sensitivity as set forth in Table VI.

Lanosterol 14α-demethylase activity in the four different strains was determined in an experiment wherein the radial growth of the different strains in media with different concentrations of inhibitor of the lanosterol 14α-demethylase is measured as a measure for the enzymatic activity. For that purpose, mycelial plugs were provided on plates with increasing concentrations of known lanosterol 14α-demethylase inhibitors (DMIs). At a higher concentration of the DMI, an increasingly smaller outgrowth of the mycelium develops. After a few days the length of the grownout mycelium filaments was determined. Calculated were the $EC_{50}$ value, the concentration of the DMI at which the length of the grown-out mycelium filaments is one-half of the outgrowth in the absence of DMI. The DMIs used were Fenarimol, Etaconazole and Imazalil. By way of check, the inhibition of growth by Benomyl was also looked at. This product inhibits mycelium growth via a different, 14 dm independent, mechanism. The results of these experiments are shown in Table VI and FIG. 6.

|  | N402 | AB2-2 | AB-D1 | AB-D1.15 |
| --- | --- | --- | --- | --- |
| Estimated 14DM copy number | "1" | "1" | "1" + ≧10 | "1" + ≧10 |
| Estimated cprA copy number | 1 | ≧10 | 1 | ≧10 |
| Benomyl | 2.27 | 3.05 | 1.93 | 3.22 |
|  | 100% | 134% | 85% | 142% |
| Fenarimol | 1.73 | 3.88 | 11.50 | 58.58 |
|  | 100% | 224% | 665% | 3270% |
| Etaconazole | 0.45 | 0.95 | 2.25 | 9.10 |
|  | 100% | 211% | 500% | 2022% |
| Imazalil | 6.43 | 9.86 | 17.57 | 66.27 |
|  | 100% | 153% | 273% | 1030% |

Table VI. Lanosterol 14α-demethylase inhibition (DMI) $EC_{50}$ values expressed in ppm. Estimated 14 DM copy number: "1" wildtype A. niger 14 DM gene, =: extra copies of the P. italicum 14 DM gene.

Media and solutions

50×AspA (1 l.)
 300 g $NaNO_3$
 26 g KCl
 76 g $KOH_2PO_4$
 18 ml KOH (10M)
 1000 * Spore elements (100 ml)
  2.2 g $ZnSO_4.7H_2O$
  1.1 g $H_3BO_3$
  0.5 g $MnCl_2.4H_2O$
  0.5 g $FeSO_4.7H_2O$
  0.17 g $CoCl_2.6H_2O$
  0.16 g $CuSO_4.5H_2O$
  0.15 g $Na_2MoO_4.2H_2O$
  5.0 g EDTA Minimal medium (500 ml)
 10 ml 50 * AspA
 10 ml 50% glucose
 0.5 ml 1000 * spore elements
 1.0 ml 1M $MgSO_4$ Complete medium
 10 ml 50 * AspA
 10 ml 50% glucose
 0.5 ml 1000 * spore elements
 1.0 ml 1M $MgSO_4$
 5.0 ml 10% Cas-amino acids
 25 ml 10% Yeast extract

We claim:
1. A recombinant DNA molecule comprising one of
(a) a nucleic acid sequence encoding a cytochrome P450 oxidoreductase having an amino acid sequence as shown in SEQ ID NO:2,
(b) a nucleic acid sequence which hybridizes under stringency conditions of 56° C. and 6X SSC with the nucleic acid sequence of (a);
(c) a nucleic acid sequence complementary with the nucleic acid sequence of (a), and

(d) a nucleic acid sequence complementary with the nucleic acid sequence of (b).

2. An RNA molecule coding for a cytochrome P450 oxidoreductase, which is derived from a DNA molecule according to claim 1.

3. A polypeptide having cytochrome P450 oxidoreductase activity, said polypeptide being coded for by a recombinant DNA molecule according to claim 1.

4. A transformed host cell which is at least transformed with a DNA molecule according to claim 1 and which is derived from a filamentous fungus.

5. A host cell according to claim 4 which is derived from a filamentous ascomycete.

6. A host cell according to claim 5 which is derived from the genus Aspergillus.

7. A host cell according to claim 6 which is derived from *Aspergillus Niger*.

8. A host cell according to claim 4 which is further transformed with a DNA molecule which codes for a p 450 cytochrome protein.

9. A host cell according to claim 8, wherein the P450 cytochrome protein is coded for by one of (a) a DNA molecule as shown in SEQ ID NO:1, and (b) a DNA molecule which hybridizes under moderately stringent conditions with a DNA molecule according to SEQ ID NO:1.

10. A process for enzymatic conversion of a substrate, comprising contacting the substrate with a filamentous fungus capable of converting said substrate and optionally recovering the conversion product formed, wherein said filamentous fungus is a recombinant filamentous fungus transformed with and expressing a recombinant DNA molecule according to claim 1.

11. A process for enzymatic conversion of a substrate, comprising contacting the substrate with an enzyme capable of converting said substrate and optionally recovering the conversion product formed, wherein said enzyme is a cytochrome P450 oxidoreductase according to claim 3.

12. A recombinant DNA molecule comprising one of (a) a part of nucleic acid sequence SEQ ID NO:1 that encodes a cytochrome P450 oxidoreductase, (b) a nucleic acid sequence which hybridizes under stringency conditions of 56° C. and 6X SSC with the nucleic acid sequence of (a), (c) a nucleic acid sequence complementary with the nucleic acid sequence of (a), and (d) a nucleic acid sequence complementary with the nucleic acid sequence of (b).

13. A process for enzymatic conversion of a substrate, comprising contacting the substrate with a filamentous fungus capable of converting said substrate and optionally recovering the conversion product formed, wherein said filamentous fungus is a recombinant filamentous fungus transformed with and expressing a recombinant DNA molecule according to claim 12.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
    ( A ) LENGTH: 3701 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO: 1:

```
TGATAACTCC TCAGCAAATC GGAGTAAACA GAAGGACAAG TCATTGGAGT ACTAAGTAGC      60

TCCGTGTCAG AGACCCGGAC AGGATCAGCT TCTCCGAACC CGAGACTCCG GGCGAAAGG     120

CCACCATCGC TCAGGCTACC ACCTGTGTTC CTTCCGTCGA TCGTCCTCCC TCGTTTCCGG    180

CTCACGGCCC CCCAAATTAT TGCGGTCTGC TTAGCAGTGG GTTCGGCCTC TCTGTTCTTC    240

CTGGATCACA CCACGGCTTA CTTTCTTATC CTTTTCCTTT TCCTTTCTTC CTTTCTTCCT    300

GTTCTCCTTT CTTCCTTTCC ACCCCCTTCT TTCTTTTAAC CCCATAGCGT CATTCTTTCT    360

TCCGTTTTAT CTTTGGTTTT GGGACGCCGC CACCTTATCT CGGTTCCTGC CTCGGTCTCC    420
```

| | | | | | |
|---|---|---|---|---|---|
| GGTGATCGCA | CCTGGATAGG | CTAAGCGTAG | GGAGGTGTGA | CATTCTTCTT | TCACCTCCTC | 480 |
| TCCTTTTCCC | GCCTCACTCC | GTTCAATCCC | CCGCTCCACC | CTTTCAGACT | CGCCATCGTA | 540 |
| TCAAGTCGGG | GCCTTTGCTT | GCGCCGCTGA | ACAGCCTCAC | CATGGCGCAA | CTCGATACCC | 600 |
| TCGATCTGGT | GGTCCTGGCG | GTGCTTTTGG | TGGGTAGCGT | GGCCTACTTC | ACCAAGGGCA | 660 |
| CCTACTGGGC | AGTTGCAAAG | ACCCGTATGC | CTCTACCGGC | CCCGCGGATG | AACGGCGCCG | 720 |
| CTAAGGCTGG | CAAGACTCGG | AACATCATTG | AGAAGATGGA | AGAAACGGGC | AAGAATTGTG | 780 |
| TTATTTTCTA | CGGATCGCAA | ACTGGAACCG | CTGAGGACTA | CGCCTCCAGA | TTGGCCAAGG | 840 |
| AAGGATCTCA | GCGCTTCGGC | CTCAAGACCA | TGGTGGCTGA | CCTCGAGGAA | TACGACTATG | 900 |
| AGAACCTGGA | CCAATTCCCG | GAGGACAAGG | TTGCGTTTTT | CGTGCTCGCC | ACCTACGGAG | 960 |
| AGGGTGAGCC | TACGGATAAT | GCTGTTGAGT | TCTACCAGTT | CTTCACCGGT | GACGACGTTG | 1020 |
| CTTTTGAGAG | CGCGTCCGCG | GACGAGAAGC | CTCTGTCCAA | GCTGAAGTAT | GTTGCTTTCG | 1080 |
| GTCTGGGTAA | CAACACTTAT | GAGCACTACA | ACGCCATGGT | TCGTCAAGTC | GATGCTGCTT | 1140 |
| TCCAGAAGCT | CGGGCCGCAG | CGTATTGGTT | CTGCTGGCGA | GGGTGATGAC | GGTGCCGGTA | 1200 |
| CAATGGAAGA | AGACTTCTTG | GCCTGGAAGG | AGCCCATGTG | GGCAGCACTG | TCGGAGTCGA | 1260 |
| TGGATCTCGA | AGAGCGTGAA | GCGGTCTACG | AACCTGTTTT | CTGCGTCACC | GAAAACGAGT | 1320 |
| CCCTGAGCCC | TGAGGACGAG | ACGGTCTATC | TTGGAGAGCC | CACCCAGAGC | CACCTTCAGG | 1380 |
| GTACTCCCAA | AGGCCCGTAC | TCTGCGCACA | ACCCCTTTAT | CGCCCCTATT | GCCGAATCTC | 1440 |
| GTGAGCTTTT | CACCGTCAAG | GATCGCAACT | GTCTGCACAT | GGAAATTAGC | ATCGCTGGAA | 1500 |
| GTAACTTGTC | CTACCAGACT | GGTGACCACA | TCGCTGTTTG | GCCCACAAAC | GCTGGTGCCG | 1560 |
| AAGTGGATCG | GTTCCTTCAG | GTCTTCGGTC | TCGAGGGCAA | GCGTGATTCG | GTCATCAACA | 1620 |
| TCAAGGGTAT | CGATGTTACG | GCCAAGGTCC | CAATCCCGAC | CCCGACCACG | TACGATGCCG | 1680 |
| CTGTTCGGTA | CTATATGGAA | GTCTGCGCCC | CTGTGTCCCG | TCAGTTTGTA | GCCACTCTGG | 1740 |
| CCGCGTTCGC | TCCGATGAGG | AAAGCAAGGC | AGAGATTGTG | CGTCTGGGTA | GCACAAGGAC | 1800 |
| TATTTCCACG | AGAAGGTCAC | CAACCAATGC | TTCAACATGC | CCAGGCTCTT | CAGAGCATCA | 1860 |
| CGTCCAAGCC | TTTCTCTGCT | GTTCCGTTCT | CTCTGCTTAT | TGAAGGCATT | ACGAAGCTGC | 1920 |
| AGCCTCGCTA | CTACTCGATC | TCTTCGTCCT | CCCTTGTCCA | GAAGGACAAG | ATCAGCATCA | 1980 |
| CGGCCGTTGT | GGAATCTGTT | CGTCTGCCCG | GTGCCTCTCA | CATGGTGAAG | GGTGTGACTA | 2040 |
| CGAATTATCT | CCTCGCGCTC | AAGCAGAAGC | AGAACGGGCG | ATCCCTCTCC | CGACCCTCAC | 2100 |
| GGCTTGACTT | ACTCCATCAC | GGTCCCCGGA | ACAAGTACGA | CGGTATCCAC | GTTCCCGTGC | 2160 |
| ATGTTCGCCA | CTCGAACTTC | AAGCTGCCCT | CTGATCCCTC | TCGGCCCATT | ATCATGGTTG | 2220 |
| GTCCTGGTAC | TGGTGTTGCT | CCTTTCCGTG | GTTTCATTCA | GGAACGTGCT | GCTTTGGCGG | 2280 |
| CCAAGGGCGA | GAAGGTTGGA | CCCACTGTTC | TCTTCTTCGG | TTGCCGCAAG | AGTGACGAGG | 2340 |
| ATTTCTTGTA | CAAGGATGAA | TGGAAGGTAA | GATATCTTTT | TTTCTTTTCC | GCAGCTACCT | 2400 |
| TCATACATCT | CGGATGCTAA | CATATCGCGA | TTCGCAGACC | TATCAGGACC | AGCTTGGAGA | 2460 |
| CAACTTGAAG | ATCATCACTG | CGTTCTCGCG | TGAGGGTCCT | CAGAAGGTCT | ACGTTCAGCA | 2520 |
| CAGACTCCGC | GAGCACTCCG | AACTTGTCAG | CGACCTTCTG | AAGCAGAAAG | CTACCTTCTA | 2580 |
| CGTCTGTGGT | GACGCTGCAA | ACATGGCTCG | CGAGGTTAAC | CTTGTGCTTG | GCCAGATCAT | 2640 |
| TGCTGCGCAG | CGTGGTCTGC | CCGCCGAGAA | GGGCGAAGAA | ATGGTCAAGC | ACATGCGTAG | 2700 |
| ACGTGGACGC | TACCAGGAAG | ATGTGTGGTC | ATAATCTTTC | AATGCATCGA | CTTTTCTTTC | 2760 |
| TTGTCTATCA | CGACGGCCTT | CTCGATCCAT | TATTTTATTT | AACGCCTAGA | TGATCTTTGC | 2820 |

| | | | | | |
|---|---|---|---|---|---|
| ATATATACTC | CGCTGATTTT | GCCTATTCAT | CTGTTTTGCT | TGGCGTGGTT | TATGTATGCC | 2880
| TAGTTTATTT | GTTTTGTGCA | CCGACCGGCC | AGCCACACAT | TGAAGTGGCT | TGAGCATGAG | 2940
| TGCGGTAGCC | AGTGTCGAAA | GAACAGGATA | GACGATCATG | ATTATTGCGG | GAACATGTTA | 3000
| TGCCATTCTG | GCATATTGA | TATCTGGTTG | CATGAGCCCA | GAGGATACGA | AAGATGAAT | 3060
| CCATATTTAA | TTTGCACAAT | ACTTTTCGCC | TTCTTCATCT | AGTAATTAAA | TTAATTGAGC | 3120
| ACTGACCGAA | CGAGCTGACA | CCTGCTGCTC | GGAATAGCCG | ACAACGCATT | GACGTGCAAG | 3180
| AGATGCATAA | TCATTACAAT | CAACAAGTAG | ACTGGTAACT | AAATCACTGA | ATACTACAGT | 3240
| TACTGCCTAC | TTTCAGCCAA | AAAGTAATAC | TGAAGATTTC | GGGGAATCAA | ATAGAAGAAA | 3300
| CATGCATAAG | CCCAACCTCG | GCAATACCGG | GAGTTAAGCA | CAGTAACCAA | AACCAAACCA | 3360
| AACTAGAACC | GGCGCGCGAC | CAGTGACCCA | TCGTCATTCC | CGGTATCAGC | AGTTCAGTCA | 3420
| GACTGGCTGG | CTAGCCCGAA | CCCAACTGCC | GCAATCATCC | ATCCATCCTC | AACCCGCCCC | 3480
| TCCCATGCCA | ACCTCTCTAC | TCCGCAGAGC | GAGGGACAAA | AAAATGAGAT | GCAGCAATTA | 3540
| ACCACGATAA | TCTAGCAAAA | AGAAAGTTAG | AAGCCGGAAG | AACATACATA | TCGCTTTTAC | 3600
| CGCTGTTCGA | CTGCGACGAC | GGGTCTTGAG | AGCAGTTCCG | CCACGTGGGC | GAAAAGCTGG | 3660
| ACTGCACACT | ACTTACGCTA | CCCTACGCTA | CCTCGGTACC | C | | 3701

( 2 ) INFORMATION FOR SEQ ID NO: 2:

( i ) SEQUENCE CHARACTERISTICS:
        ( A ) LENGTH: 693 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( x i ) SEQUENCE DESCRIPTION: SEQ ID NO: 2:

```
Met Ala Gln Leu Asp Thr Leu Asp Leu Val Val Leu Ala Val Leu Leu
 1               5                  10                  15

Val Gly Ser Val Ala Tyr Phe Thr Lys Gly Thr Tyr Trp Ala Val Ala
                20                  25                  30

Lys Thr Arg Met Pro Leu Pro Ala Pro Arg Met Asn Gly Ala Ala Lys
                35                  40                  45

Ala Gly Lys Thr Arg Asn Ile Ile Glu Lys Met Glu Glu Thr Gly Lys
    50                  55                  60

Asn Cys Val Ile Phe Tyr Gly Ser Gln Thr Gly Thr Ala Glu Asp Tyr
65                  70                  75                  80

Ala Ser Arg Leu Ala Lys Glu Gly Ser Gln Arg Phe Gly Leu Lys Thr
                85                  90                  95

Met Val Ala Asp Leu Glu Glu Tyr Asp Tyr Glu Asn Leu Asp Gln Phe
                100                 105                 110

Pro Glu Asp Lys Val Ala Phe Phe Val Leu Ala Thr Tyr Gly Glu Gly
            115                 120                 125

Glu Pro Thr Asp Asn Ala Val Glu Phe Tyr Gln Phe Phe Thr Gly Asp
    130                 135                 140

Asp Val Ala Phe Glu Ser Ala Ser Ala Asp Glu Lys Pro Leu Ser Lys
145                 150                 155                 160

Leu Lys Tyr Val Ala Phe Gly Leu Gly Asn Asn Thr Tyr Glu His Tyr
                165                 170                 175
```

-continued

| | | | | | | | | | | | | | |
|---|---|---|---|---|---|---|---|---|---|---|---|---|---|
| Asn | Ala | Met | Val 180 | Arg | Gln | Val | Asp 185 | Ala | Ala | Phe | Gln | Lys 190 | Leu | Gly | Pro |
| Gln | Arg | Ile 195 | Gly | Ser | Ala | Gly 200 | Glu | Gly | Asp | Asp 205 | Gly | Ala | Gly | Thr | Met |
| Glu | Glu | Asp 210 | Phe | Leu | Ala | Trp 215 | Lys | Glu | Pro | Met 220 | Trp | Ala | Ala | Leu | Ser |
| Glu 225 | Ser | Met | Asp | Leu 230 | Glu | Glu | Arg | Gln | Ala 235 | Val | Tyr | Glu | Pro | Val 240 | Phe |
| Cys | Val | Thr | Glu | Asn 245 | Glu | Ser | Leu | Ser | Pro 250 | Glu | Asp | Glu | Thr | Val 255 | Tyr |
| Leu | Gly | Glu | Pro 260 | Thr | Gln | Ser | His | Leu 265 | Gln | Gly | Thr | Pro | Lys 270 | Gly | Pro |
| Tyr | Ser | Ala 275 | His | Asn | Pro | Phe | Ile 280 | Ala | Pro | Ile | Ala 285 | Glu | Ser | Arg | Glu |
| Leu | Phe 290 | Thr | Val | Lys | Asp | Arg 295 | Asn | Cys | Leu | His | Met 300 | Glu | Ile | Ser | Ile |
| Ala 305 | Gly | Ser | Asn | Leu | Ser 310 | Tyr | Gln | Thr | Gly | Asp 315 | His | Ile | Ala | Val | Trp 320 |
| Pro | Thr | Asn | Ala | Gly 325 | Ala | Glu | Val | Asp | Arg 330 | Phe | Leu | Gln | Val | Phe 335 | Gly |
| Leu | Glu | Gly | Lys 340 | Arg | Asp | Ser | Val | Ile 345 | Asn | Ile | Lys | Gly | Ile 350 | Asp | Val |
| Thr | Ala | Lys 355 | Val | Pro | Ile | Pro | Thr 360 | Pro | Thr | Thr | Tyr 365 | Asp | Ala | Ala | Val |
| Arg | Tyr 370 | Tyr | Met | Glu | Val | Cys 375 | Ala | Pro | Val | Ser | Arg 380 | Gln | Phe | Val | Ala |
| Thr 385 | Leu | Ala | Ala | Phe | Ala 390 | Pro | Met | Arg | Lys | Ala 395 | Arg | Gln | Arg | Leu | Cys 400 |
| Val | Trp | Val | Ala | Gln 405 | Gly | Leu | Phe | Pro | Arg 410 | Glu | Gly | His | Gln | Pro 415 | Met |
| Leu | Gln | His | Ala 420 | Gln | Ala | Leu | Gln | Ser 425 | Ile | Thr | Ser | Lys | Pro 430 | Phe | Ser |
| Ala | Val | Pro 435 | Phe | Ser | Leu | Leu | Ile 440 | Glu | Gly | Ile | Thr | Lys 445 | Leu | Gln | Pro |
| Arg | Tyr 450 | Tyr | Ser | Ile | Ser | Ser 455 | Ser | Ser | Leu | Val | Gln 460 | Lys | Asp | Lys | Ile |
| Ser 465 | Ile | Thr | Ala | Val | Val 470 | Glu | Ser | Val | Arg | Leu 475 | Pro | Gly | Ala | Ser | His 480 |
| Met | Val | Lys | Gly | Val 485 | Thr | Thr | Asn | Tyr | Leu 490 | Leu | Ala | Leu | Lys | Gln 495 | Lys |
| Gln | Asn | Gly | Arg 500 | Ser | Leu | Ser | Arg | Pro 505 | Ser | Arg | Leu | Asp | Leu 510 | Leu | His |
| His | Gly | Pro 515 | Arg | Asn | Lys | Tyr | Asp 520 | Gly | Ile | His | Val 525 | Pro | Val | His | Val |
| Arg | His 530 | Ser | Asn | Phe | Lys | Leu 535 | Pro | Ser | Asp | Pro | Ser 540 | Arg | Pro | Ile | Ile |
| Met 545 | Val | Gly | Pro | Gly | Thr 550 | Gly | Val | Ala | Pro | Phe 555 | Arg | Gly | Phe | Ile | Gln 560 |
| Glu | Arg | Ala | Ala | Leu 565 | Ala | Ala | Lys | Gly | Glu 570 | Lys | Val | Gly | Pro | Thr 575 | Val |
| Leu | Phe | Phe | Gly 580 | Cys | Arg | Lys | Ser | Asp 585 | Glu | Asp | Phe | Leu | Tyr 590 | Lys | Asp |
| Glu | Trp | Lys 595 | Thr | Tyr | Gln | Asp | Gln 600 | Leu | Gly | Asp | Asn | Leu 605 | Lys | Ile | Ile |

```
            Thr  Ala  Phe  Ser  Arg  Glu  Gly  Pro  Gln  Lys  Val  Tyr  Val  Gln  His  Arg
                 610                 615                      620

Leu  Arg  Glu  His  Ser  Glu  Leu  Val  Ser  Asp  Leu  Leu  Lys  Gln  Lys  Ala
            625                      630                 635                           640

Thr  Phe  Tyr  Val  Cys  Gly  Asp  Ala  Ala  Asn  Met  Ala  Arg  Glu  Val  Asn
                                645                      650                      655

Leu  Val  Leu  Gly  Gln  Ile  Ile  Ala  Ala  Gln  Arg  Gly  Leu  Pro  Ala  Glu
                           660                      665                      670

Lys  Gly  Glu  Glu  Met  Val  Lys  His  Met  Arg  Arg  Arg  Gly  Arg  Tyr  Gln
                      675                      680                      685

Glu  Asp  Val  Trp  Ser
            690
```

( 2 ) INFORMATION FOR SEQ ID NO: 3:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO: 3:

CCGGAATTCC ARACNGGNAC NGCNGARGA          29

( 2 ) INFORMATION FOR SEQ ID NO: 4:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO: 4:

CCGGAATTCG GNGANCCNAC NGAYAAYGC          29

( 2 ) INFORMATION FOR SEQ ID NO: 5:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO: 5:

CGCGGATCCG GNCCNAYNAD DATNAC          26

( 2 ) INFORMATION FOR SEQ ID NO: 6:

( i ) SEQUENCE CHARACTERISTICS:

(A) LENGTH: 26 base pairs
(B) TYPE: nucleic acid
(C) STRANDEDNESS: unknown
(D) TOPOLOGY: unknown (ii) MOLECULE TYPE: other nucleic acid (iii) HYPOTHETICAL: NO (iv) ANTI-SENSE: NO (xi) SEQUENCE DESCRIPTION: SEQ ID NO: 6:

GCGGGATCCT SYTGNACRTA NACYTT    26

(2) INFORMATION FOR SEQ ID NO: 7:

(i) SEQUENCE CHARACTERISTICS:
(A) LENGTH: 26 base pairs
(B) TYPE: nucleic acid
(C) STRANDEDNESS: unknown
(D) TOPOLOGY: unknown (ii) MOLECULE TYPE: other nucleic acid (iii) HYPOTHETICAL: NO (iv) ANTI-SENSE: NO (xi) SEQUENCE DESCRIPTION: SEQ ID NO: 7:

CGCGGATCCG GNCCDATCAT DATNAC    26

(2) INFORMATION FOR SEQ ID NO: 8:

(i) SEQUENCE CHARACTERISTICS:
(A) LENGTH: 13 base pairs
(B) TYPE: nucleic acid
(C) STRANDEDNESS: unknown
(D) TOPOLOGY: unknown (ii) MOLECULE TYPE: other nucleic acid (iii) HYPOTHETICAL: NO (iv) ANTI-SENSE: NO (xi) SEQUENCE DESCRIPTION: SEQ ID NO: 8:

CCACGCTACC CAC    13

(2) INFORMATION FOR SEQ ID NO: 9:

(i) SEQUENCE CHARACTERISTICS:
(A) LENGTH: 14 base pairs
(B) TYPE: nucleic acid
(C) STRANDEDNESS: unknown
(D) TOPOLOGY: unknown (ii) MOLECULE TYPE: other nucleic acid (iii) HYPOTHETICAL: NO (iv) ANTI-SENSE: NO (xi) SEQUENCE DESCRIPTION: SEQ ID NO: 9:

GAGGCATACG GGTC    14